(12) United States Patent
Singh et al.

(10) Patent No.: US 10,544,109 B2
(45) Date of Patent: Jan. 28, 2020

(54) PROCESS FOR THE PREPARATION OF XYLENE LINKED CYCLAM COMPOUNDS

(71) Applicant: FRESENIUS KABI ONCOLOGY LTD., New Delhi (IN)

(72) Inventors: Hemant Kumar Singh, Haryana (IN); Sandeep Kumar, Haryana (IN); Ghanashyam Madhukar Sonavane, Haryana (IN); Vishal Handa, Haryana (IN); Chandan Kumar Gupta, Haryana (IN); Sunil Sanghani, Haryana (IN); Potru Sivaiah, Haryana (IN); Saswata Lahiri, Haryana (IN); Walter Cabri, Milan (IT); Nitin Gupta, Haryana (IN)

(73) Assignee: Fresenius Kabi Oncology Ltd., New Delhi (IN)

( * ) Notice: Subject to any disclaimer, the term of this patent is extended or adjusted under 35 U.S.C. 154(b) by 0 days.

(21) Appl. No.: 15/757,259

(22) PCT Filed: Sep. 1, 2016

(86) PCT No.: PCT/IB2016/055215
§ 371 (c)(1),
(2) Date: Mar. 2, 2018

(87) PCT Pub. No.: WO2017/037639
PCT Pub. Date: Mar. 9, 2017

(65) Prior Publication Data
US 2018/0244635 A1    Aug. 30, 2018

(30) Foreign Application Priority Data
Sep. 2, 2015    (IN) .......................... 2758/DEL/2015

(51) Int. Cl.
*C07D 257/02*    (2006.01)
*C07C 69/78*    (2006.01)
*C07D 487/22*    (2006.01)

(52) U.S. Cl.
CPC ............ *C07D 257/02* (2013.01); *C07C 69/78* (2013.01); *C07D 487/22* (2013.01)

(58) Field of Classification Search
None
See application file for complete search history.

(56) References Cited

FOREIGN PATENT DOCUMENTS

| IN | 25/2013 | 6/2013 |
|---|---|---|
| WO | WO 93/12096 A1 | 6/1993 |
| WO | WO 00/28987 A1 | 5/2000 |
| WO | WO 02/26721 A1 | 4/2002 |
| WO | WO 2014/125499 A1 | 8/2014 |

OTHER PUBLICATIONS

Le Baccon et al., "Bis-aminals : efficient tools for bis-macrocycle synthesis," *New J. Chem* 25: 1168-1174 (2001).
European Patent Office, International Search Report in International Application PCT/IB2016/055215 (dated Dec. 23, 2016).
European Patent Office, Written Opinion in International Application PCT/IB2016/055215 (dated Dec. 23, 2016).
International Bureau of WIPO, International Preliminary Report on Patentability in International Application PCT/IB2016/055215 (dated Mar. 6, 2018).
Ciampolini et al., "Dinickel and dicopper complexes with N,N-linked bis(cyclam) ligands. An ideal system for the investigation of electrostatic effects on the redox behavior of pairs of metal ions," *Inorg. Chem.* 26(21): 3527-3533 (1987).
Boschetti et al., "Regioselective N-Functionalization of Tetraazacycloalkanes," *J. Org. Chem.* 70(18): 7042-7053 (2005).

*Primary Examiner* — Zinna Northington Davis
(74) *Attorney, Agent, or Firm* — Leydig, Voit & Mayer, Ltd.

(57) ABSTRACT

The present invention relates to an improved process for the preparation of xylene linked cyclam compounds. More particularly the invention provides a process for preparation of high purity plerixafor which does not involve the use of expensive chemicals, hazardous reagents or tedious purification techniques. Invention also provides novel intermediate useful for preparation of desired compound in high purity.

15 Claims, No Drawings

PROCESS FOR THE PREPARATION OF XYLENE LINKED CYCLAM COMPOUNDS

CROSS-REFERENCE TO RELATED APPLICATIONS

This patent application is the U.S. national stage of International Patent Application No. PCT/IB2016/055215, filed on Sep. 1, 2016, which claims the benefit of Indian Patent Application No. 2758/DEL/2015, filed Sep. 2, 2015, the disclosures of which are incorporated herein by reference in their entireties for all purposes.

FIELD OF THE INVENTION

The present invention relates to a process for the preparation of xylene linked cyclam compounds, more particularly, it relates to an improved process for preparing 1,1'-[1,4-phenylenebis (methylene)]-bis [1,4,8,11-tetraazacyclotetra decane] and its intermediates. In another aspect, the present invention relates to intermediates used in the above processes.

BACKGROUND OF THE INVENTION

The compound 1,1'-[1,4-phenylenebis (methylene)]-bis [1,4,8,11-tetraazacyclo tetradecane], also known as plerixafor is represented by the Formula (I):

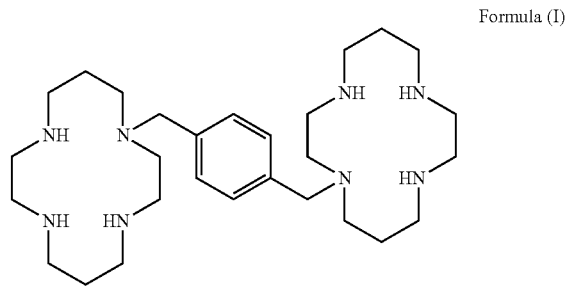 [SMILES: c1cc(CN2CCCNCCNCCCNCC2)ccc1CN1CCCNCCNCCCNCC1]

Formula (I)

Plerixafor (marketed under the trade name Mozobil, Genzyme Corporation) is a hematopoietic stem cell mobilizer and is inhibitor of the CXCR4 chemokine receptors. It was approved by the U.S. Food and Drug Administration (FDA) on 15 Dec. 2008 to mobilize hematopoietic stem cells (HSCs) to the peripheral blood for collection and subsequent autologous transplantation in patients with non-Hodgkin's lymphoma and multiple myeloma.

Plerixafor, as represented by Formula (I) was first reported by Ciampolini et al. in Inorg. Chem, 1987, 26 (21), pp 3527-3533.

Various processes for the preparation of plerixafor have been described in literature. Conventionally, the compound of formula (I) is prepared by selective functionalization of the cyclam ring, followed by reaction with α,α'-dihalo-p-xylene and dimerization. The product is deprotected to obtain the compound of formula (I) which is further purified by recrystallization in various solvents.

WO 93/12096 describes the synthesis of different xylene linked polyamine macrocyclic compounds as explained above, wherein the cyclam ring is tosyl protected and reacted with an activated xylene diol intermediate to obtain an intermediate which is purified by column chromatography and deprotected to obtain the final product.

A similar process for the synthesis of compound of formula (I) is described in the WO 00/28987. The synthetic scheme is depicted below as scheme-1:

Scheme-1

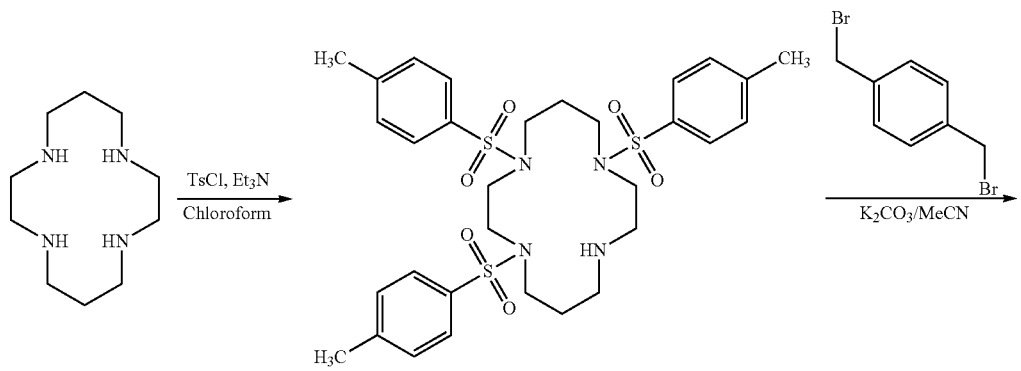

-continued

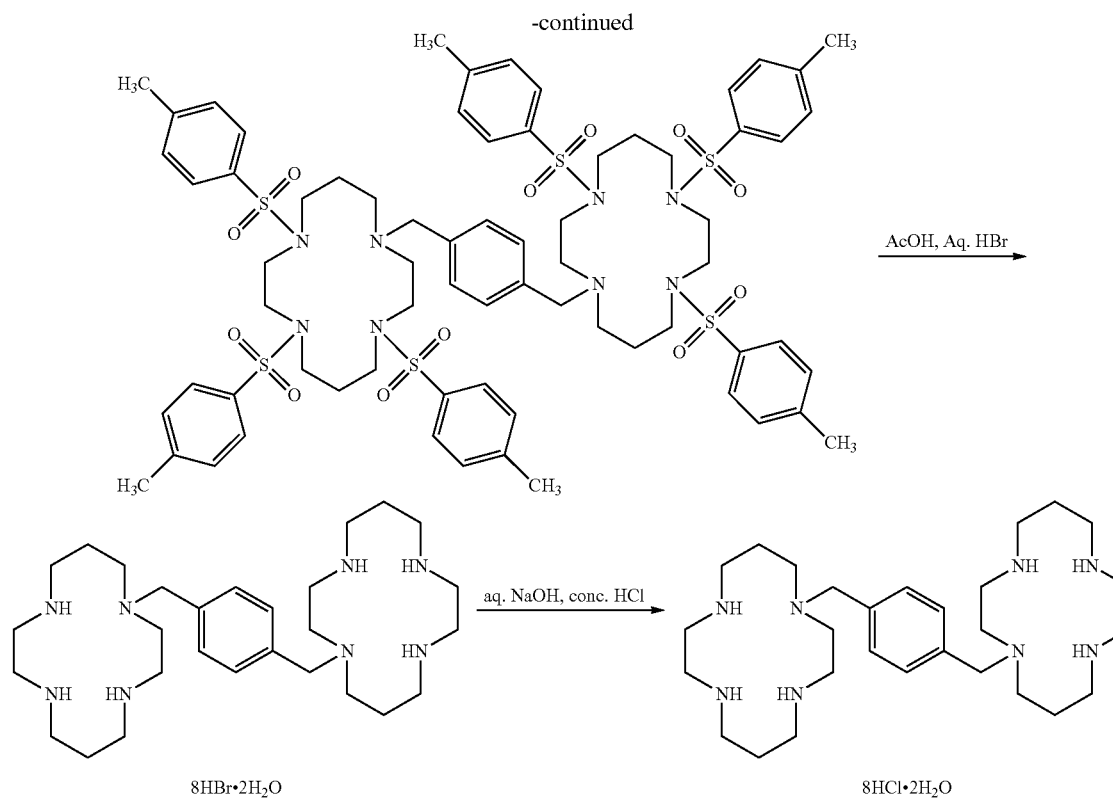

8HBr·2H₂O       8HCl·2H₂O

Cyclam is reacted with p-toluene sulfonyl chloride in the presence of triethylamine to obtain tris-(p-toluenesulfonyl)-1,4,8,11-tetraazacyclotetradecane in 33% yield. This tosyl protected cyclam ring is reacted with α,α'-dibromo-p-xylene in the presence of base in solvent at reflux temperature to give 1,1'-[1,4-phenylenebis(methylene)]-bis[4,8,11-tris-(p-toluene sulfonyl)-1,4,8,11-tetraazacyclotetradecane which is purified by chromatography. Finally this intermediate is subjected to hydrolysis in a mixture of acetic acid and hydrobromic acid to afford the final compound as octahydrobromide salt, the purity of which is not mentioned.

Further, WO 2014/125499 also describes a similar process for the preparation of plerixafor. Cyclam is protected with tosyl groups in the presence of triethylamine in dichloromethane. The yield is 36.4%. The resulting compound was reacted with α,α'-dibromo-p-xylene in the presence of potassium carbonate in dimethylformamide. The yield is 40%. Deprotection of this intermediate in the presence of acetic acid and hydrobromic acid gives plerixafor octahydrobromide dihydrate in 90.3% yield.

The above mentioned synthetic processes do not afford the intermediate compounds in good yield or purity. Column chromatography is required to purify the intermediates and therefore a significant amount of yield is lost.

In WO 02/26721A1, the authors disclose a process for the preparation of plerixafor base using ethyl trifluoroacetate as protecting reagent instead of p-toluene sulfonyl chloride. The reaction scheme is summarized below in scheme-2.

Scheme-2

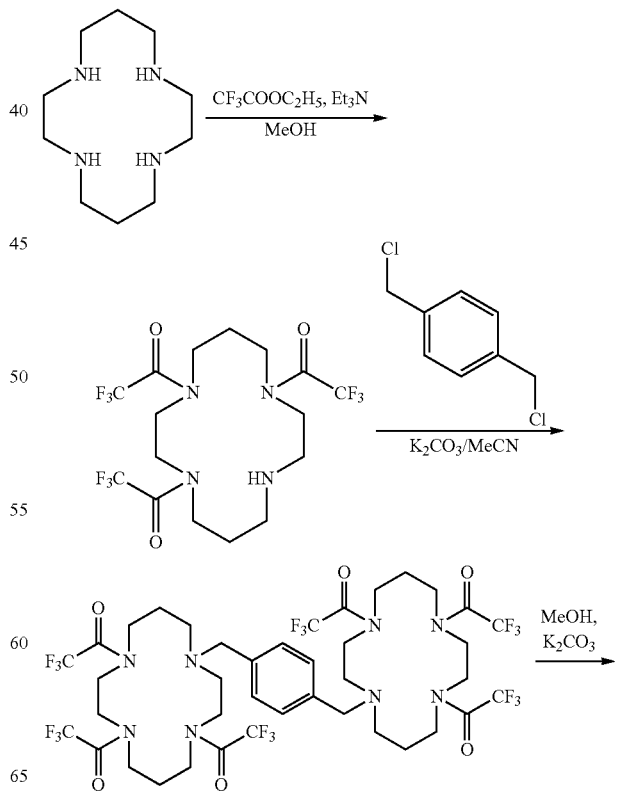

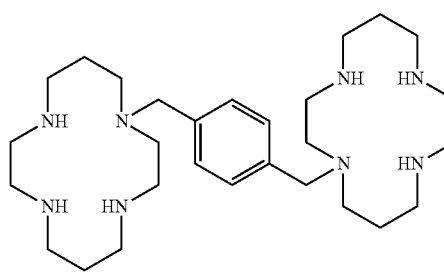
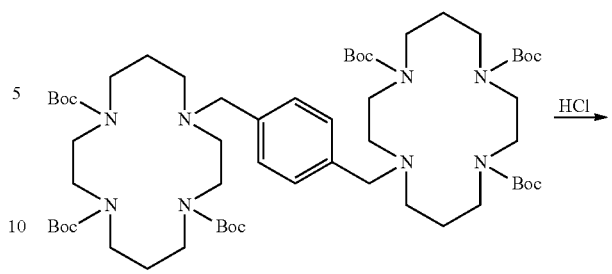

Cyclam is reacted with ethyl trifluoroacetate in the presence of triethylamine in methanol to give tris trifluoroacetyl cyclam. The resulting compound is isolated by column chromatography technique. The yield is 92.5%. The purity of the compound is not mentioned. The compound is coupled with α,α'-dichloro-p-xylene in the presence of potassium carbonate and potassium iodide in acetonitrile at reflux temperature to get the product in 85% yield. Here also compound purity is not mentioned. Deprotection of trifluoro acetyl group of the product is carried out by treatment with potassium carbonate in methanol to afford plerixafor base in 86% yield. The compound is isolated from toluene but the purity is not mentioned.

This process gives better yield but the purity of the intermediates or of plerixafor base is not mentioned. Also, column chromatography is required for the isolation of the tris trifluoroacetyl cyclam intermediate. Column chromatography, needless to say, is a tedious process which makes this route unfit for commercial purposes.

Indian patent application IN2011CH2459 describes a process for the preparation of plerixafor using tert-butoxycarbonyl as the protecting group. The reaction scheme is summarized below in scheme 3:

Scheme-3

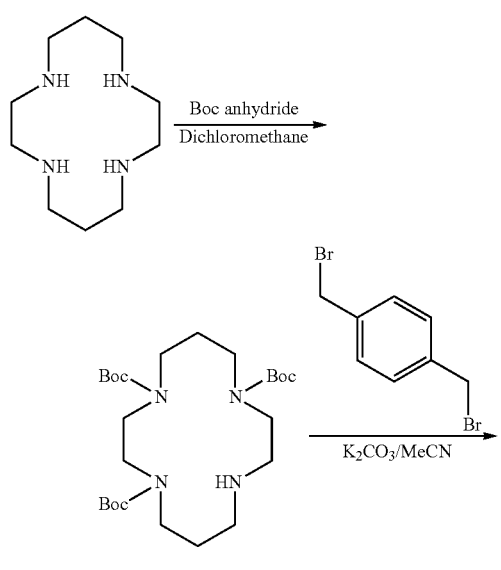

wherein, "Boc" means tert-butoxycarbonyl. Cyclam is reacted with di-tert-butyl dicarbonate in methylene chloride to give tris-Boc protected cyclam. The compound is reacted with α,α'-dibromoxylene in the presence of potassium carbonate in acetonitrile to yield 1,1'-xylyl-bis [4,8,11-tris(tert-butoxycarbonyl)-1,4,8,11-tetraazacyclotetradecane]. The resulting compound is subjected to treatment with 1N hydrochloric acid and later with sodium hydroxide to obtain plerixafor, which is crystallized from acetone. The purity of final compound or intermediates is not mentioned and the overall yield is extremely low.

The inventors of the present invention have found that in all the above mentioned processes the purity of intermediate compounds is very low leading to significant yield losses during purification. A possible reason for such high amount of impurity formation appears to be the presence of four secondary nitrogen atoms in cyclam, out of which only three need to be protected. But during the reaction of cyclam with p-toluene sulfonyl chloride, Boc anhydride or ethyltrifluoroacetate, mono, di, tri and tetraprotected cyclam is formed. The structures of these are as shown below:

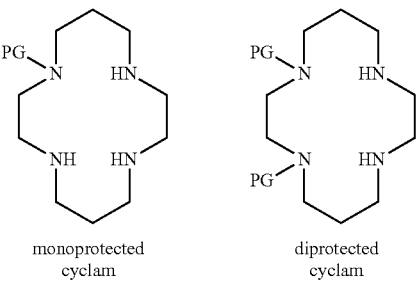

monoprotected cyclam      diprotected cyclam

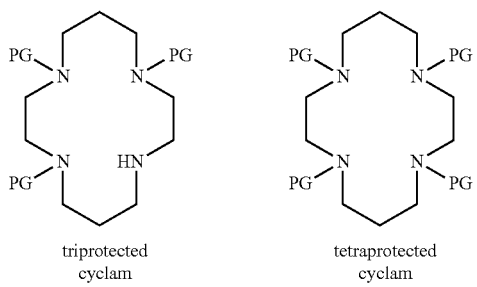

triprotected cyclam     tetraprotected cyclam wherein PG represents a protecting group like Tosyl or Boc etc.

Such mono- or di-protected cyclam rings will give side reactions leading to further impurities while the tetra protected cyclam will remain unreacted as an impurity in the subsequent steps. These impurities are difficult to remove and result in low yield and purity of further steps as well.

New J. Chem. 2001, 25, 1168-1174, describes an alternative process for the preparation of plerixafor. The cyclam ring is protected with the help of glyoxal, the protected cyclam ring is then reacted with dibromo-p-xylene to yield an intermediate which is deprotected with the help of hydroxylamine hydrochloride and sodium ethoxide to yield the final compound. The overall synthesis is shown in scheme-4:

Scheme-4

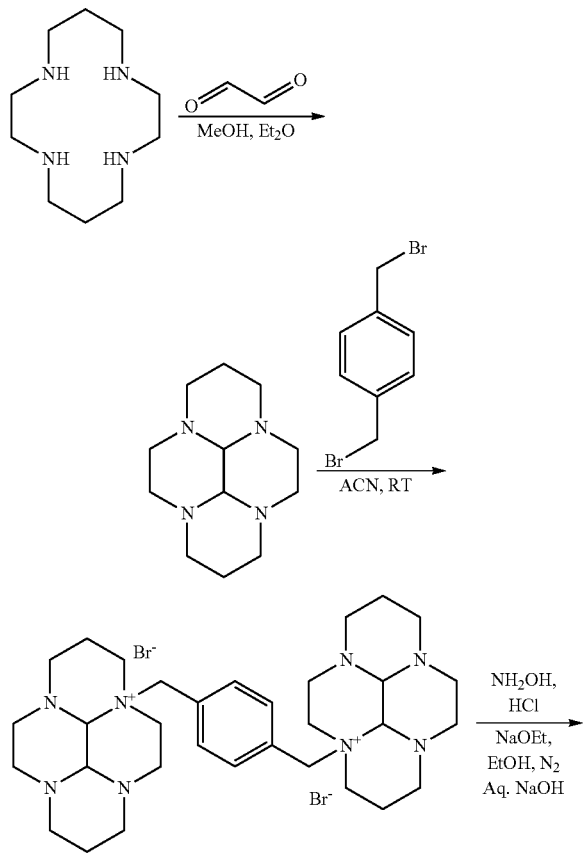

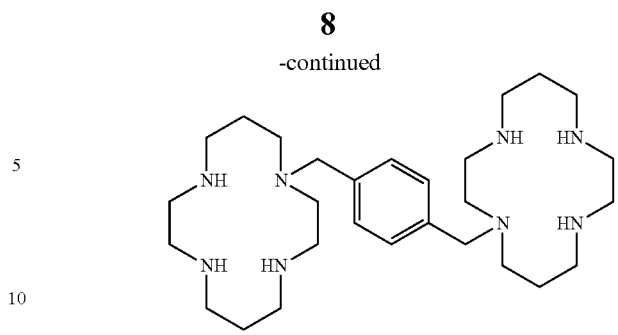

The glyoxal protection of the cyclam ring prevents the formation of mono, di or tetra-protected impurities and therefore it is expected that the yield and purity of the final compound be better than those of the other processes.

However, it was found that the purity of plerixafor obtained via this process is very low. It was further found by the inventors that the glyoxal protected cyclam is a low melting and hygroscopic solid which is impossible to isolate or purify.

Any process generated impurities are carried forward to the next stages leading to an impure final compound.

Also, the final deprotection reaction involves the use of the hazardous, difficult to handle and hygroscopic reagent, sodium ethoxide. The use of strong reagents like sodium ethoxide leads to large amounts of impurity formation. Thus the final compound obtained by this process has very low purity.

Various inorganic bases have been described in literature for the removal of bis-aminal bridge from the cyclam moiety. J. Org. Chem., 2005, 70, 7042-7053 describes the use of sodium hydroxide for the deprotection of cyclam rings from plerixafor. But no information about the quality or purity of the product is mentioned.

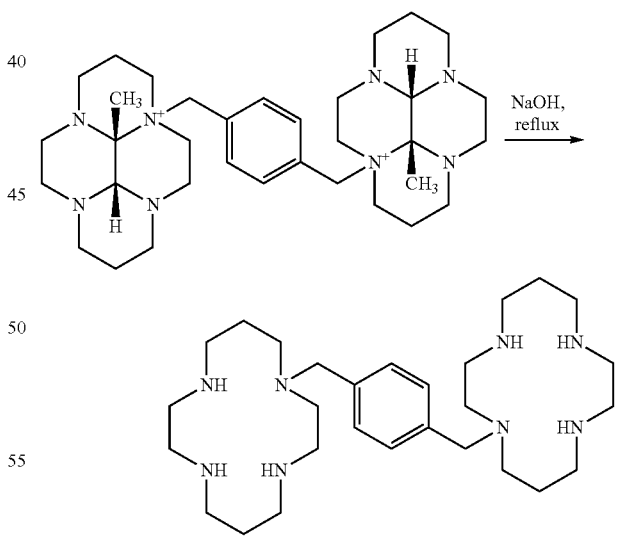

From the foregoing, it is apparent that the reported methods for the preparation of plerixafor suffer from one or more of the following drawbacks:
(a) extensive column chromatography needed to purify the intermediates used in the process,
(b) low yields obtained due to the formation of impurities, and
(c) use of hazardous and moisture sensitive reagents.

Thus, there still remains the need to formulate an efficient, simple and industrially viable synthetic process which can overcome the drawbacks of the prior art and which provides plerixafor and its intermediates free of impurities.

OBJECT OF THE INVENTION

It is an objective of the present invention to overcome the above-mentioned drawbacks of the prior art.

It is another objective of the present invention to provide an improved and commercially viable process for the synthesis of plerixafor without the use of expensive and hazardous reagents.

It is a further objective of the present invention to provide useful intermediates for the synthesis of plerixafor.

SUMMARY OF THE INVENTION

The present invention provides an improved, commercially viable process for the preparation of plerixafor. The process of the present invention is easy and cost effective when implemented on industrial scale.

In first aspect, the present invention relates to a process for the preparation of a compound of formula (I),

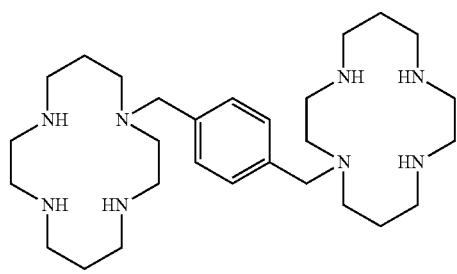

Formula (I)

comprising, the reaction of the compound of formula (VII),

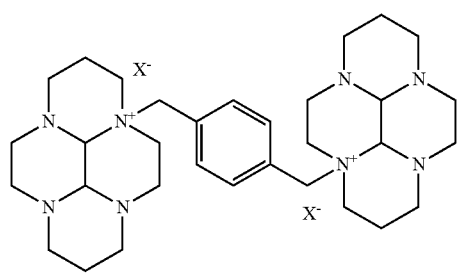

Formula (VII)

wherein X⁻ is ion of a leaving group
with hydroxylamine or hydroxylamine hydrochloride in the presence of tertiary amine or tertiary alkoxide.

In another aspect, the present invention provides a process for the preparation of a compound of formula (I),

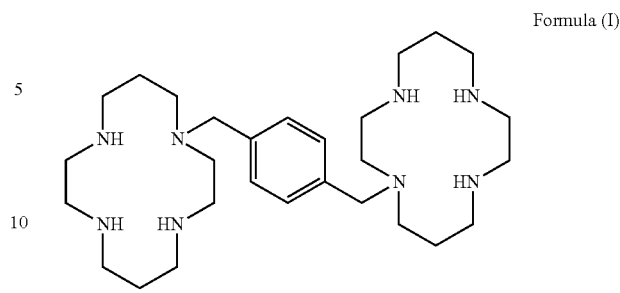

Formula (I)

comprising the steps of:
a) reacting a compound of formula (II),

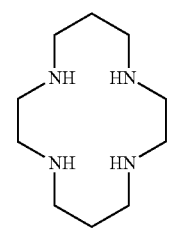

Formula (II)

with a compound of formula (III),

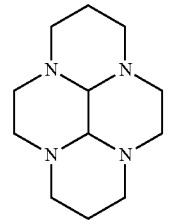

Formula (III)

to obtain a compound of formula (IV) or its salts,

Formula (IV)

b) reacting the compound of formula (IV) with a compound of formula (V),

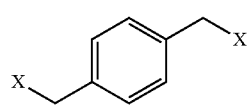

Formula (V)

wherein X is a leaving group to obtain a compound of formula (VII),

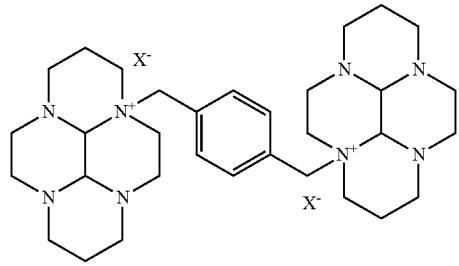

Formula (VII)

wherein X⁻ is ion of the leaving group, and c) reacting the compound of formula (VII) with hydroxylamine or hydroxylamine hydrochloride in the presence of tertiary amine or tertiary alkoxide.

Another aspect of the present invention is to provide a process for the preparation of compound of formula (I) using the compound of formula (VI).

Another aspect of the invention is to provide a compound of formula (VI),

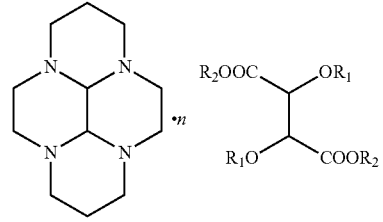

Formula (VI)

wherein n=1, 2 and $R_1$, $R_2$ may be independently selected from hydrogen, optionally substituted alkyl, aryl, acyl, alkylaryl or aralkyl group.

In another aspect, the present invention provides a process for the preparation of the compound of formula (VI).

DETAILED DESCRIPTION OF THE INVENTION

In one aspect, a process for the preparation of a compound of formula (I),

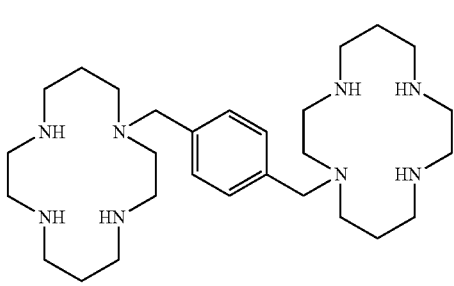

Formula (I)

comprising, the reaction of the compound of formula (VII),

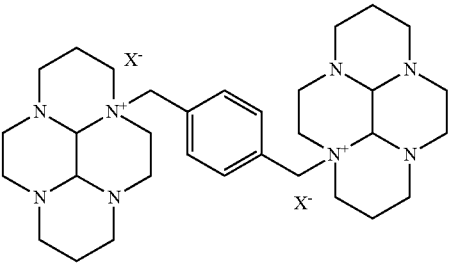

Formula (VII)

wherein X⁻ is ion of a leaving group
with hydroxylamine or hydroxylamine hydrochloride in the presence of tertiary amine or tertiary alkoxide is provided.

The reaction may optionally be carried out in the presence of a solvent.

The solvent used in this reaction may be selected from the group comprising of water, alcohols like methanol, ethanol, isopropyl alcohol or halogenated hydrocarbons like dichloromethane, chloroform or esters like methyl acetate, ethyl acetate or ketones like methyl ethyl ketone, acetone, isobutyl ketone or hydrocarbons like hexane, heptanes, toluene or polar apotic solvents, polar protic solvents, ethers or mixtures thereof. Preferably the reaction is carried out in the presence of, methanol, ethanol or isopropyl alcohol. Most preferably the reaction is carried out in the presence of isopropyl alcohol.

The tertiary amine may be selected from triethylamine or diisopropylethylamine. Tertiary alkoxides may be selected from sodium tertiary butoxide or potassium tertiary butoxide.

The methods for the preparation of plerixafor reported in prior art involve the use of tedious purification techniques or the use of hazardous chemicals and the product obtained has low yield and purity.

The inventors have found that the above mentioned process, which comprises of deprotection reaction with hydroxylamine or hydroxylamine hydrochloride in the presence of tertiary amine or tertiary alkoxide, provides plerixafor in high yield and purity.

Another aspect of the present invention is to provide a process for the preparation of a compound of formula (I),

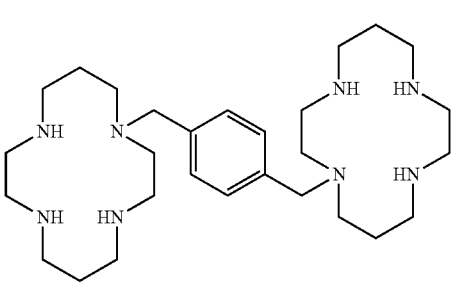

Formula (I)

comprising the steps of:
a) reacting a compound of formula (II),

Formula (II)

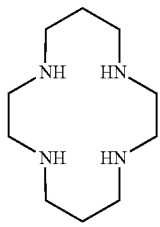

with a compound of formula (II),

Formula (III)

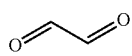

to obtain a compound of formula (IV) or its salts,

Formula (IV)

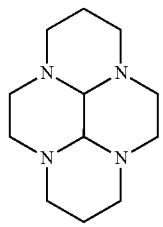

b) reacting the compound of formula (IV) with a compound of formula (V),

Formula (V)

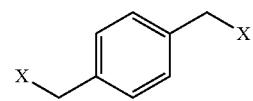

wherein X is a leaving group
to obtain a compound of formula (VII),

Formula (VII)

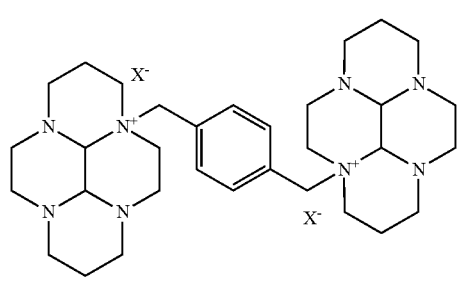

wherein X⁻ is ion of the leaving group, and
c) reacting the compound of formula (VII) with hydroxylamine or hydroxylamine hydrochloride in the presence of tertiary amine or tertiary alkoxide.

The product obtained by this process has higher yield and purity and there is no need for the use of column chromatography or expensive and hazardous chemicals.

In one embodiment, the reaction of compound of formula (II) with the compound of formula (III) in step a) is carried out in the presence of a solvent.

In a preferred embodiment, the solvent used in step a) may be selected from the group comprising of water, alcohols like methanol, ethanol, isopropyl alcohol or halogenated hydrocarbons like dichloromethane, chloroform or esters like methyl acetate, ethyl acetate or ketones like methyl ethyl ketone, acetone, isobutyl ketone or hydrocarbons like hexane, heptanes, toluene or polar apotic solvents, polar protic solvents, ethers or mixtures thereof. Preferably, the reaction is carried out in the presence of methanol, ethanol or isopropyl alcohol. Most preferably the reaction is carried out in the presence of methanol.

As discussed above, the reaction of compound of formula (IV) with a compound of formula (V) is carried out to produce a compound of formula (VII) in step b). In the compound of formula (V), X is a leaving group, preferably, a halogen or mesyl or tosyl, more preferably the leaving group is a halogen and most preferably the leaving group is bromine.

The reaction may be carried out in the presence of solvents selected from the group comprising of halogenated hydrocarbons like dichloromethane, dichloroethane or chloroform, polar aprotic solvents like dimethylformamide, dimethylacetamide or dimethylsulfoxide, nitriles like acetonitrile or propionitrile. Preferably, the reaction is carried out in the presence acetonitrile, propionitrile, dimethylformamide or dimethylsulfoxide. Most preferably, the reaction is carried out in the presence of acetonitrile.

In step c) of the first embodiment, the compound of formula (VII) is reacted with hydroxylamine or hydroxylamine hydrochloride in the presence of tertiary amine or tertiary alkoxide.

The tertiary amine may be selected from triethylamine or diisopropylethylamine. Tertiary alkoxides may be selected from sodium tertiary butoxide or potassium tertiary butoxide.

It was found that the purity and yield of the product are much improved when hydroxylamine or hydroxylamine hydrochloride is used in the presence of tertiary amines or tertiary alkoxides, unlike the methods reported in literature which lead to the formation of impure product.

Data on purity of the product obtained using hydroxylamine hydrochloride reagent in the presence of various bases is given in table-1.

TABLE 1

| S. No | Base used | Reagent used | HPLC Purity of crude product (%) |
|---|---|---|---|
| 1 | Triethylamine | Hydroxylamine hydrochloride | 91.31 |
| 2 | Diisopropylethylamine | Hydroxylamine hydrochloride | 92.56 |
| 3 | Potassium tert. butoxide | Hydroxylamine hydrochloride | 84.93 |
| 4 | Sodium ethoxide | Hydroxylamine hydrochloride | 62.78 |
| 5 | Without base | Hydroxylamine hydrochloride | No product formed |

The solvent used in this reaction may be selected from the group comprising of water, alcohols like methanol, ethanol, isopropyl alcohol or halogenated hydrocarbons like dichloromethane, chloroform or esters like methyl acetate, ethyl acetate or ketones like methyl ethyl ketone, acetone, isobutyl ketone or hydrocarbons like hexane, heptanes, toluene or polar apotic solvents, polar protic solvents, ethers or mixtures thereof. Preferably the reaction is carried out in the presence of, methanol, ethanol or isopropyl alcohol. Most preferably the reaction is carried out in the presence of isopropyl alcohol.

In another embodiment, the reaction of a salt of compound of formula (IV) with a compound of formula (V) to obtain a compound of formula (VII) is provided. The salt of compound of formula (IV) is a compound of formula (VI),

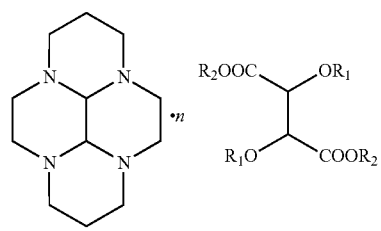

Formula (VI)

wherein n is 1 or 2; and $R_1$, $R_2$ may be independently selected from hydrogen, optionally substituted alkyl, aryl, acyl, alkylaryl or aralkyl group.

The present invention also relates to a compound of formula (VI).

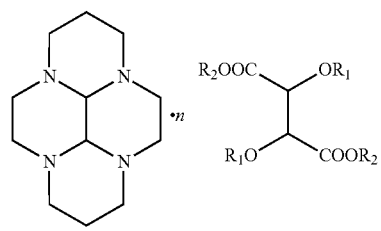

Formula (VI)

wherein R1 and R2 and n are as defined above.

The compound of formula (VI) is a salt of compound of formula (IV) which is a hygroscopic, low melting compound that cannot be purified except by column chromatography. But the substituted tartaric acid salts can be isolated and purified.

In a preferred embodiment, the compound of formula (VI) is a compound of formula (X),

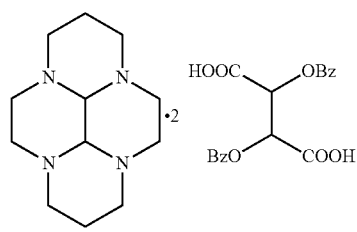

Formula (X)

wherein Bz is benzoyl group.

The compound of formula (X) is the Dibenzoyl-L-tartaric acid salt of compound of formula (IV). The compound of formula (IV), glyoxal protected cyclam, is a low melting, hygroscopic solid which is difficult to isolate or purify. Further various salts of this compound are also difficult to isolate as either these salts do not precipitate and if they precipitate, they are highly soluble in most organic solvents and water and therefore cannot be purified.

However, the substituted tartaric acid salts, especially dibenzoyl-L-tartaric acid salt is unique as this salt can be isolated, purified and also shows greater stability compared to the free base or other salts of this compound. Various acids, organic and inorganic, were used to isolate the stable salt of compound of formula (IV).

For example: hydrochloric acid, tartaric acid, p-toluenesulfonic acid, acetic acid, benzoic acid etc. But only the substituted tartaric acids, represented by formula (VIII), were found to give stable, non-hygroscopic salts of compound of formula (IV).

Another aspect of the present invention is to provide a process for the preparation of compound of formula (I) using the compound of formula (VI).

Yet another aspect of the present invention is to provide a process for the preparation of the compound of formula (VI), comprising the reaction of a compound of formula (IV),

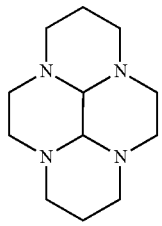

Formula (IV)

with a compound of formula (VIII),

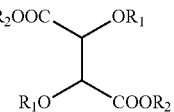

Formula (VIII)

wherein $R_1$ and $R_2$ may be independently selected from hydrogen, optionally substituted alkyl, aryl, acyl, alkylaryl or aralkyl group to obtain the compound of formula (VI).

The reaction may be carried out in the presence of suitable solvent. Suitable solvent may be selected from a group comprising of water, alcohols like methanol, ethanol, isopropyl alcohol or halogenated hydrocarbons like dichloromethane, chloroform or esters like methyl acetate, ethyl acetate or ketones like methyl ethyl ketone, acetone, isobutyl ketone or hydrocarbons like hexane, heptanes, toluene or polar apotic solvents, polar protic solvents, ethers or mixtures thereof. Preferably the reaction is carried out in the presence of acetone or methyl acetate or ethyl acetate. Most preferably the reaction is carried out in the presence of ethyl acetate.

Preferably, the compound of formula (VIII) is a compound of formula (IX),

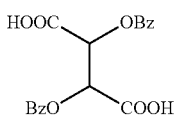

wherein Bz is benzoyl.

In a further aspect, a compound of formula (VI) is provided,

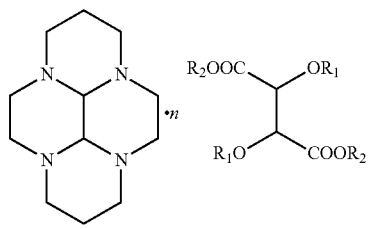

wherein n=1, 2 and $R_1$, $R_2$ may be independently selected from hydrogen, optionally substituted alkyl, aryl, acyl, alkylaryl or aralkyl group.

Preferably, the compound of formula (VI) is a compound of formula (X),

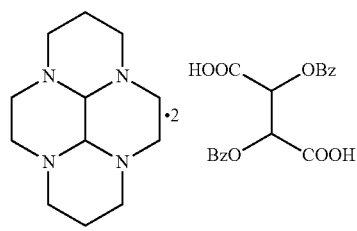

wherein Bz is benzoyl group.

EXPERIMENTAL

Detailed experimental parameters suitable for the preparation of plerixafor according to the present invention are provided by the following examples, which are intended to be illustrative and not limiting of all possible embodiments of the invention.

Example-1

Preparation of (2R, 3R)-2,3-bis(benzoyloxy)butanedioic acid-decahydro-1H,6H-3a,5a,8a,10a-tetraazapyrene (Compound of Formula VI)

To a stirred solution of 1,4,8,11-tetraazacyclotetradecane (50.0 g, 0.249 mole) in methanol (1625 ml) at −5° C. was added a solution of glyoxal (44.2 g, 0.304 mole) in methanol (250 ml) dropwise. After complete addition the reaction temperature was raised to 30° C. and stirred for 4 hrs. Methanol was distilled off and the residue was stirred with ethyl acetate (750 ml) and filtered through celite bed. The filtrate was added dropwise to a stirred solution of dibenzoyl-L-tartaric acid (205.7 g, 0.574 mole) in ethyl acetate (1500 ml) and the reaction mixture was stirred for 3 hrs at 30° C. The reaction mixture was filtered and solid obtained was washed with ethyl acetate. The crude product was dried under vacuum at 55° C. for 20 hrs. The crude product was again slurry washed with water and dried to give the title compound.

Yield: 78.9% (185 g)
GC Purity: 99.87%

Example-2

Preparation of 3a,3a'-(benzene-1,4-diyldimethanediyl)bisdecahydro-1H,6H-5a,8a,10a-triaza-3a-azoniapyrene Dibromide (Compound of Formula VII)

To a stirred solution of (2R, 3R)-2, 3-bis(benzoyloxy) butanedioic acid-decahydro-1H,6H-3a,5a,8a,10a-tetraazapyrene (1000 g, 1.065 mole) in dichloromethane (10000 ml) was added a solution of potassium carbonate (588.8 g, 4.260 mole) in water at room temperature. The reaction mixture was stirred for 15 minutes and the layers were separated. The solvent was distilled off and acetonitrile (4500 ml) and α,α'-dibromo-p-xylene (115.3 g, 0.436 mole) were added. The reaction mixture was stirred at room temperature for 30 hrs. The solid obtained was filtered and dried under vacuum and finally recrystallized from a mixture of methanol and IPA to obtain the title compound.

Yield: 72.3% (273.0 g)
HPLC Purity: 98.65%

Example-3

Preparation of Plerixafor

To a stirred solution of hydroxylamine hydrochloride (760 g, 10.937 mole) in isopropyl alcohol (5000 ml) was added triethylamine (1071 g, 10.584 mole) at room temperature and the reaction mixture was stirred for 1.5 hrs. To this was added the product of example-2 (250 g, 0.353 mole) and the reaction mixture was heated to 90° C. and stirred at same temperature for 24 hrs. The solvent was distilled off and water (2500 ml) was added. An aqueous solution of sodium hydroxide was added and reaction mass was stirred. The layers were allowed to separate and dichloromethane was added to the organic layer. The organic layer was then washed with water. The organic solvent was distilled off and product was crystallized from toluene.

Yield: 52% (92.4 g)
HPLC Purity: 99.25%

Example-4

Purification of Plerixafor

To a stirred mixture of acetone (2250 ml) and water (250 ml) was added crude plerixafor (250 g) and reaction mixture was heated to 60° C. and stirred for 15 minutes. The solution obtained was filtered through 5 micron filter paper and the filtrate was stirred at 20° C. for 2.5 hrs. The solution was further cooled to 0° C. and stirred for 2 hrs. The solid obtained was filtered and dried under vacuum.

Yield: 91.6% (229 g)
HPLC Purity: 99.80%
$^1$HNMR (400 MHz, CDCl3) δ: 1.646-1.656 (m, 4H), 1.842-1.852 (m, 4H), 2.446-2.456 (m, 4H), 2.517-2.531 (m, 4H), 2.545-2.560 (m, 4H), 2.602-2.615 (m, 4H), 2.627-2.652 (m, 4H), 2.663-2.710 (m, 4H), 2.720-2.736 (m, 4H), 2.750-2.804 (m, 4H), 2.966 (s, 4H), 3.352 (s, 2H), 3.511 (s, 4H), 7.276 (s, 4H).

We claim:

1. A process for preparing a compound of formula (I),

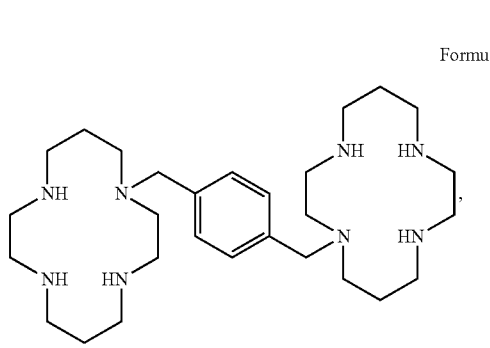

Formula (I)

the process comprising reacting a compound of formula (VII),

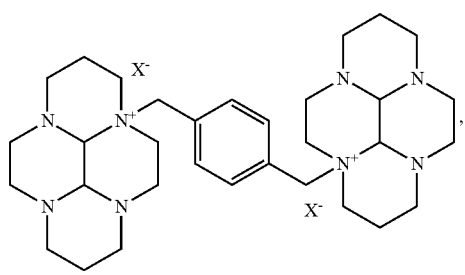

Formula (VII)

wherein X⁻ is an ion of a leaving group, with hydroxylamine or hydroxylamine hydrochloride in the presence of a tertiary amine, wherein the tertiary amine is other than the compound of formula (VII), or a tertiary alkoxide.

2. The process according to claim 1, further comprising the steps of:

a) reacting a compound of formula (II),

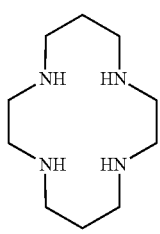

Formula (II)

with a compound of formula (III),

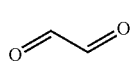

Formula (III)

to obtain a compound of formula (IV) or a salt thereof,

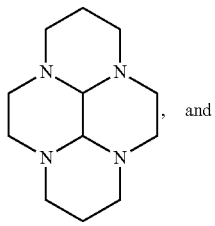

Formula (IV)

, and b) reacting the compound of formula (IV) or a salt thereof with a compound of formula (V),

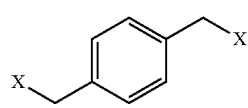

Formula (V)

wherein X is a leaving group, to obtain the compound of formula (VII).

3. The process according to claim 1, wherein the leaving group is a halogen.

4. The process according to claim 1, wherein the tertiary amine is trimethylamine or diisopropylethylamine, and the tertiary alkoxide is potassium tertiary butoxide.

5. The process according to claim 2, wherein step a) is carried out in the presence of a solvent, which comprises methanol, ethanol or isopropyl alcohol.

6. The process according to claim 2, wherein step b) is carried out in the presence of a solvent, which comprises acetonitrile, propionitrile, dimethylformamide or dimethylsulfoxide.

7. The process according to claim 1, wherein the reaction is carried out in the presence of a solvent, which comprises methanol, ethanol or isopropyl alcohol.

8. The process according to claim 2, wherein the compound of formula (IV) or salt thereof is a compound of formula (VI),

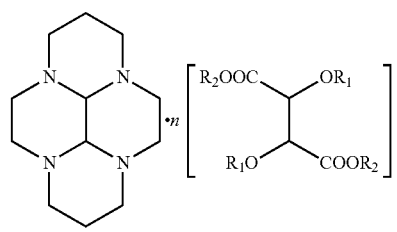

Formula (VI)

wherein n is 1 or 2; and $R_1$ and $R_2$ are independently hydrogen, optionally substituted alkyl, aryl, acyl, alkylaryl or aralkyl.

9. The process according to claim 8, wherein the compound of formula (VI),

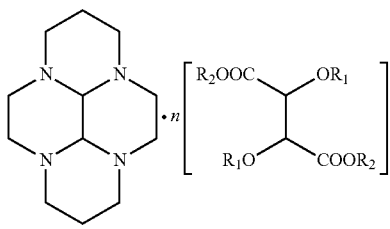

Formula (VI)

is prepared by a process comprising reacting a compound of formula (IV),

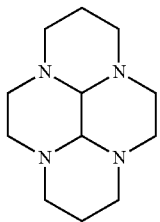

Formula (IV)

with a compound of formula (VIII),

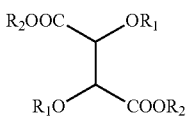

Formula (VIII)

wherein $R_1$ and $R_2$ are independently hydrogen, optionally substituted alkyl, aryl, acyl, alkylaryl or aralkyl, to obtain the compound of formula (VI).

10. The process according to claim 9, wherein the compound of formula (VIII) is a compound of formula (IX),

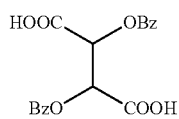

Formula (IX)

wherein Bz is benzoyl.

11. The process according to claim 8, wherein the compound of formula (VI) is a compound of formula (X),

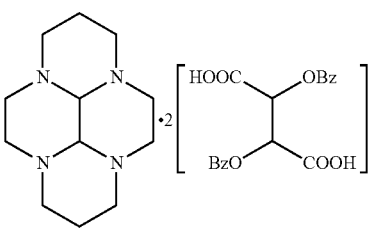

Formula (X)

wherein, Bz is benzoyl.

12. The process according to claim 1, comprising reacting the compound of formula (VII) with hydroxylamine or hydroxylamine hydrochloride in the presence of the tertiary amine other than the compound of formula (VII).

13. The process according to claim 12, wherein the tertiary amine is trimethylamine or diisopropylethylamine.

14. The process according to claim 1, comprising reacting the compound of formula (VII) with hydroxylamine or hydroxylamine hydrochloride in the presence of the tertiary alkoxide.

15. The process according to claim 13, wherein the tertiary alkoxide is potassium tertiary butoxide.

* * * * *